United States Patent [19]

Prussak

[11] Patent Number: 5,447,859
[45] Date of Patent: Sep. 5, 1995

[54] METHOD FOR THE PURIFICATION OR REMOVAL OF RETROVIRUSES USING SULFATED CELLULOSE

[75] Inventor: Charles E. Prussak, San Diego, Calif.

[73] Assignee: Viagene, San Diego, Calif.

[21] Appl. No.: 93,436

[22] Filed: Jul. 16, 1993

[51] Int. Cl.$^6$ .......................... C12N 7/02; C02F 1/42
[52] U.S. Cl. .................................. 435/239; 536/33; 536/59; 210/660
[58] Field of Search .............. 435/239; 536/59, 33; 210/660

[56] References Cited

U.S. PATENT DOCUMENTS

| | | | |
|---|---|---|---|
| 3,528,963 | 9/1970 | Reid et al. | 536/59 |
| 3,720,659 | 3/1973 | Guiseley et al. | 536/59 |
| 4,064,342 | 12/1977 | Saika et al. | 536/59 |
| 4,138,287 | 2/1979 | Andersson et al. | 435/239 |
| 4,423,208 | 12/1983 | Grandics | 17/536 |
| 4,515,714 | 5/1985 | Kawahara et al. | 39/260 |
| 4,563,303 | 1/1986 | Ginnaga et al. | 7/260 |
| 4,724,146 | 2/1988 | Kino et al. | 39/424 |
| 4,724,210 | 2/1988 | Oka et al. | 435/239 |
| 4,725,546 | 2/1988 | Sakamoto et al. | 435/239 |
| 4,725,547 | 2/1988 | Sakamoto et al. | 435/239 |
| 4,855,416 | 8/1989 | Usher | 536/112 |
| 5,221,669 | 6/1993 | Anand et al. | 514/58 |

FOREIGN PATENT DOCUMENTS

WO88/02776 4/1988 WIPO .
WO89/09643 10/1989 WIPO .
WO91/02049 2/1991 WIPO .

OTHER PUBLICATIONS

Brochure–"Purify Virus Without Centrifuge and Recover Up to 100%," Amicon, Publication No. 866, W. R. Grace & Co., Conn.

EEC Regulatory Document, Note for Guidance, "Validation of Virus Removal and Inactivation Procedures," *Biologicals* 19:247–251, 1991.

L. Kestens et al., "HIV antigen detection in circulating immune complexes," *Journal of Virological Methods* 31:67–76, 1991.

Erik Lycke et al., "Binding of herpes simplex virus to cellular heparan, an initial step in the adsorption process," *Journal of General Virology* 72:1131–1137, 1991.

Baba, M. et al., "Mechanism of inhibitory effect of dextran sulfate and heparin on replication of human immunodeficiency virus in vitro, "Proc. Natl. Acad. Sci. USA 85:6132–6136, 1988.

"Matrex Cellufine Sulfate for Concentration, Purification, and Depyrogenation of Virus, Viral/Microbial Antigens and Heparin-binding Proteins," Amicon, *Technical Data*, Publication No. 845, 1988, W. R. Grace & Co.

"Matrex Cellufine Sulfate Media & the Virus Recovery System," Amicon, Publication No. 1–351, 1989, W. R. Grace & Co., Conn.

Hiroaki Mitsuya et al., "Dextran Sulfate Suppression of Viruses in the HIV Family: Inhibition of Virion Binding to CD4+Cells," *Science* 240:646–649, 1988.

P. F. O'Neil and E. S. Balkovic, "Virus Harvesting and Affinity-Based Liquid Chromatography," *Bio/Technology* 11:173–178, 1993.

G. F. Rimmelzwaan et al., "Purification of infectious canine parvovirus from cell culture by affinity chromatography with monoclonal antibodies," Journal of Virological Methods 15:313–322, 1987.

(List continued on next page.)

*Primary Examiner*—Marian Knode
*Assistant Examiner*—L. Blaine Lankford
*Attorney, Agent, or Firm*—Seed and Berry

[57] ABSTRACT

Methods and compositions useful for the separation of viruses, including retroviruses and vital vectors, from preparations are disclosed. Sulfated oligosaccharides with at least about 6 μmoles sulfate per gram of oligosaccharide are provided. In one aspect, a sulfated oligosaccharide of the present invention may be used in the purification of a virus, such as a lipid envelope virus. The present invention also discloses methods for the removal of a contaminating virus from a preparation, such as biologic therapeutics.

5 Claims, No Drawings

OTHER PUBLICATIONS

Charles J. Sherr and George J. Todaro, "Purification and Assay of Murine Leukemia Viruses," *Methods in Enzymology* 58:424, 1979.

Pierre Trépanier et al., "Concentration of Human Respiratory Synctial Virus Using Ammonium Sulfate, Polyethylene glycol or Hollow Fiber Ultrafiltration," *J. Virol. Meth.* 3:201–211, 1981.

"Virus Recovery System for Concentration and Purification of Virus and Viral Antigens," Amicon, *Technical Data,* Publication No. 895, 1989, W. R. Grace & Co., Conn.

T. Uryu et al., "Sulfated Alkyl Oligosaccharides with Potent inhibitory Effects On Human Immunodeficiency Virus Infection," *Biochemical Pharmacology* 43 (11):2385–2392, 1992.

METHOD FOR THE PURIFICATION OR REMOVAL OF RETROVIRUSES USING SULFATED CELLULOSE

TECHNICAL FIELD

The present invention relates generally to the removal of viruses, including retroviruses, from biological and chemical preparations. This invention is more particularly related to methods for the removal of viruses from preparations using highly sulfated carbohydrate-based matrices; and the use of such methods to purify viruses or to decontaminate preparations containing viruses.

BACKGROUND OF THE INVENTION

Viruses have in the past, and will into the foreseeable future, continue to significantly affect living organisms, whether animal, plant or otherwise. Viruses are perhaps most well known as infectious agents capable of replicating inside eukaryotic or prokaryotic cells. For thousands of years, viruses have caused diseases in epidemic proportion as well as on less dramatic scales. More recently, the possibilities for putting viruses or portions of viruses to use in ways beneficial to living organisms have been uncovered and are expanding. For example, non-virulent viruses are considered a safe and efficient means for delivering DNA molecules to cells. In this regard, there is a demand for purified viruses. Initial virus harvests from culture systems usually contain the virus as part of a complex mixture which includes host proteins and nucleic acids. Traditional means for concentrating and purifying viruses include ultracentrifugation and density gradient separation methods. These methodologies are time-consuming, cumbersome and present potential health hazards. Other procedures, such as polyethylene glycol or ammonium sulfate precipitation, may also lead to the loss of viral infectivity. Due to the difficulties in the current approaches to concentrating and purifying viruses, there is a need in the art for improved methods.

Viral contamination of preparations, such as biologic products, is a serious problem. For example, use of HIV contaminated blood for transfusions has had tragic consequences for the recipients. Potential viral contamination of a biological may arise from the source material or as adventitious agents introduced by the culture process. Due to the difficulties in the current approaches to preparing virus-free preparations, there is a need in the an for improved methods.

The present invention fulfills these needs, and further provides other related advantages.

SUMMARY OF THE INVENTION

Briefly stated, the present invention provides compositions and methods to separate lipid envelope viruses, e.g., retroviruses, from preparations. In one aspect, sulfated oligosaccharides are provided wherein the sulfated oligosaccharides possess at least about 6 μmoles sulfate per gram of cellulose. In one embodiment, the sulfated oligosaccharide possesses from about 6 to 15 μmoles sulfate per gram of cellulose. In another embodiment, the sulfated oligosaccharide possesses greater than about 10 μmoles sulfate per gram of cellulose.

In another aspect, the present invention provides methods for the purification of a virus from contaminating substances. In one embodiment, the method comprises the steps of:
  (a) contacting a preparation containing a lipid envelope virus with a sulfated oligosaccharide, the sulfated oligosaccharide possessing from about 6 to 15 μmoles sulfate per gram of oligosaccharide, under conditions and for a time sufficient for the lipid envelope virus to bind to the sulfated oligosaccharide;
  (b) separating the portion of the preparation which is not bound to the sulfated oligosaccharide from the sulfated oligosaccharide; and
  (c) eluting the bound lipid envelope virus from the sulfated oligosaccharide, thereby recovering the lipid envelope virus substantially free of substrates unable to bind to the sulfated oligosaccharide.

In another embodiment, the method comprises the steps of:
  (a) contacting a preparation containing a retrovirus with a sulfated oligosaccharide, said sulfated oligosaccharide possessing from about 6 to 15 μmoles sulfate per gram of oligosaccharide, under conditions and for a time sufficient for said retrovirus to bind to said sulfated oligosaccharide;
  (b) separating the portion of the preparation which is not bound to said sulfated oligosaccharide from said sulfated oligosaccharide; and
  (c) eluting said bound retrovirus from said sulfated oligosaccharide, thereby recovering said retrovirus substantially free of substances unable to bind to said sulfated oligosaccharide.

In another aspect, the present invention provides methods for the removal of a contaminating virus from a preparation. In one embodiment, the method comprises the steps of:
  (a) contacting a preparation suspected of containing a lipid envelope virus with a sulfated oligosaccharide, the sulfated oligosaccharide possessing at least about 6 μmoles sulfate per gram of oligosaccharide, under conditions and for a time sufficient to permit a lipid envelope virus to bind to the sulfated oligosaccharide; and
  (b) separating the portion of the preparation which is not bound to the sulfated oligosaccharide from the sulfated oligosaccharide.

In another embodiment, the method comprises the steps of:
  (a) contacting a preparation suspected of containing a retrovirus with a sulfated oligosaccharide, the sulfated oligosaccharide possessing at least about 6 μmoles sulfate per gram of oligosaccharide, under conditions and for a time sufficient to permit a retrovirus to bind to the sulfated oligosaccharide; and
  (b) separating the portion of the preparation which is not bound to the sulfated oligosaccharide from the sulfated oligosaccharide.

In yet another aspect, the present invention provides methods and compositions for delivering a retrovirus. In one embodiment, the method comprises administering to a warm-blooded animal a retrovirus bound to a sulfated oligosaccharide, the sulfated oligosaccharide possessing at least about 6 μmoles sulfate per gram of oligosaccharide. The compositions comprise a sulfated oligosaccharide wherein the oligosaccharide contains at least about 6 μmoles sulfate per gram of oligosaccharide and has a retrovirus bound thereto.

Other aspects of the :invention will become evident upon reference to the following detailed description.

DETAILED DESCRIPTION OF THE INVENTION

As noted above, the present invention is directed toward compositions and methods useful for the separation of viruses from preparations or delivery to warm-blooded animals. As disclosed within the present invention, moderately to highly sulfated oligosaccharides are useful for a variety of purposes, including for the purification of viruses, for the removal of vital contaminants in preparations, and for the delivery of viruses.

The sulfated oligosaccharides of the present invention include both moderately sulfated and highly sulfated oligosaccharides. As used herein, moderately sulfated oligosaccharides refers to oligosaccharides having at least about 6 μmoles sulfate per gram of oligosaccharide to about 15 μmoles sulfate per gram. Highly sulfated oligosaccharides contain greater than about 15 μmoles sulfate per gram of oligosaccharides. Generally, the maximum level of sulfation is about 20 μmoles. Suitable oligosaccharides include alkyl oligosaccharides, with cellulose, heparin and agarose as preferred oligosaccharides. A crystalline cellulose which retains its native structure is particularly preferred.

It will be evident to those of ordinary skill in the art that a variety of oligosaccharides may be prepared in moderately or highly sulfated forms. The sulfated oligosaccharides of the present invention are typically prepared by chemical treatment of an oligosaccharide. In chemical synthesis, a sulfating reagent such as chlorosulfonic acid or anhydrous sulfuric acid may be used to effect sulfation. For example, chlorosulfonic acid is added dropwise to pyridine while a cold temperature is maintained, generally less than 0° C. The mixture is heated to a temperature below the boiling point of pyridine, generally between 65°–70° C., and an oligosaccharide is added. The temperature is maintained and the reaction mixture stirred to keep the oligosaccharide suspended in the liquid phase. The reaction is permitted to proceed for several hours, generally for 4–6 hours. Highly sulfated oligosaccharides may be prepared by including additional sulfating reagent and increasing the reaction time. The completed reaction mixture is cooled, generally to about room temperature (e.g., 25° C.), and neutralized with base, generally 10% NaOH. The neutralized gel can be collected, e.g., by filtration (such as on a sintered glass filter). It is desirable to wash the gel with copious amounts of a salt containing buffer, generally a NaCl containing buffer, to remove residual base and to prepare the gel for sample application. Sulfated oligosaccharides may be added, for example, to a column for chromatographic procedures or used directly in batch procedures.

The maximal binding capacity of a sulfated oligosaccharide for a virus may be determined. Briefly, a 1 ml column of sulfated oligosaccharide is poured. Following a low salt wash (50 mM to <0.5M), a 1 ml aliquot of a viral solution (preferably containing a known titer of virus) is added. The column effluent is collected. This process is repeated until the virus saturates all column binding sites and is eluted directly in the column void ("viral breakthrough"). By measuring the amount of virus in the samples applied to the column and the volume of virus sample applied before viral breakthrough, the relative capacity of the sulfated oligosaccharide can be determined. Once the binding capacity of the column is determined, the total amount of sulfated oligosaccharide needed to bind the total viral content of a sample can be determined. It is preferable that no more than 75% of the total binding capacity of the sulfated oligosaccharide be used.

The binding strength of a virus for a sulfated oligosaccharide may be determined. Briefly, a 2 ml column of sulfated oligosaccharide is poured. Following a low salt wash, a 1 ml aliquot of a viral solution (preferably containing a known titer of virus) is added. The column effluent is collected. Two ml samples of buffered solutions containing increasingly larger amount of salts are added. The column eluent is collected. By assaying the column eluent for both viral content and ionic strength, the minimal salt concentration required to bind the bound virus can be determined.

One use of a sulfated oligosaccharide of the present invention is in the purification of a virus. A preferred use is in the purification of retroviral-based gene therapy vectors. In general, a moderately sulfated oligosaccharide is preferred because further increasing the amount of sulfate groups on the oligosaccharide also increases the ionic strength needed to remove a bound virus.

Any virus that is capable of binding to a sulfated oligosaccharide is a candidate for purification. It will be evident to those of ordinary skill in the art that the capacity of a candidate virus to bind to a sulfated oligosaccharide may be readily tested. For example, a viral containing preparation may be contacted with a sulfated oligosaccharide, the oligosaccharide washed to remove unbound virus, and the amount of virus in the wash compared to the amount of virus in the initial preparation. As used herein, the term "virus" includes DNA viruses, RNA viruses, retroviruses, and viral vectors, such as retroviral vectors. Suitable viruses include lipid envelope viruses, such as murine leukemia virus (MLV), HIV, and murine retrovirus. Preferred viruses include retroviruses. Particularly preferred viruses include MLV, herpes, and hepatitis D.

A virus may be purified from a variety of types of preparations. For example, a cell free supernate which contains a virus can be the preparation. Alternatively, a virus may be purified from other preparations, such as blood products.

A sulfated oligosaccharide of the present invention may be used in a variety of formats in the purification of a virus. For example, a sulfated oligosaccharide may be placed in a column. The sulfated oligosaccharide is the solid phase column matrix. A viral containing preparation is passed through the column and the virus adsorbs to the sulfated oligosaccharide. It will be appreciated by those of ordinary skill in the art that optimization of column performance is dependent upon sample volumes and flow rates. Substances in the preparation that do not bind to the sulfated oligosaccharide will pass through the column. For example, albumin, pyrogens and DNA do not bind. It may be desirable to wash the column one or more times to ensure that all unbound substances have been removed. The virus which is bound to the sulfated oligosaccharide is de-adsorbed from the column by using a high ionic strength buffer (i.e., about 0.5M–3M salt in a buffered solution). Prior to elution of the virus, it may be desirable to wash the column with another buffer solution (having an ionic strength greater than the application strength, but less than that required to elute the virus) in order to remove any substances weakly bound to the column. It will be evident to those of ordinary skill in the art that use of a sulfated oligosaccharide of the present invention in the purification of a virus may be performed in combination with other purification techniques, such as standard chromatographic techniques. Such techniques include, for example, ion exchange chromatography and gel filtration chromatography. In a multi-step procedure, a step utilizing a sulfated oligosaccharide may be the initial step, final step, or be interposed between other steps, and may be repeated.

An alternative to use of a sulfated oligosaccharide of the present invention in column chromatography is the use in a batch format. For batch applications, a sulfated oligosaccharide can be added directly to a viral containing preparation. To maximize the interaction of the sulfated oligosaccharide with a virus, the reaction mixture should be gently agitated. Following virus adsorption to the sulfated cellulose (e.g., 30 minutes at room temperature with gentle stirring), the portion of the preparation which is not bound can be separated from the virus containing sulfated oligosaccharide in a variety of ways. For example, the sulfated oligosaccharide may be separated by centrifugation (e.g., $1000 \times g$ for 5 min.), filtration or settling (e.g., 2 hr. at $1 \times g$). The virus which is bound to the sulfated oligosaccharide is de-adsorbed by using a high ionic strength buffer. In addition, as described above, it may be desirable to wash the sulfated oligosaccharide with one or more solutions prior to elution of the virus.

Monitoring for the presence of virus in column or batch eluates may be performed by a variety of techniques. Such techniques include plaque assays and colony forming unit (CFU) assays, such as those described herein.

Another use of a sulfated oligosaccharide of the present invention is the removal of a virus which is contaminating a preparation. Such preparations include biological samples, such as antibody samples, blood, biologic products, and other biopharmaceutical products. Although moderately sulfated oligosaccharides may be used, highly sulfated oligosaccharides are preferred. A highly sulfated oligosaccharide is particularly advantageous for the bulk removal of contaminating viruses because of its larger capacity for binding viruses. Further, since increasing the amount of sulfate groups on an oligosaccharide also may substantially influence the binding of the virus, use of a highly sulfated oligosaccharide may be more desirable. However, since increasing the amount of sulfate groups on an oligosaccharide also increases the ionic strength necessary to remove a virus from the sulfated oligosaccharide, it may be desirable to discard, rather than attempt to regenerate, very highly sulfated oligosaccharide that contains a virus bound thereto.

Similar to use in the purification of a virus, a sulfated oligosaccharide of the present invention may be used in a variety of formats for the removal of a contaminating virus from a preparation. For example, a sulfated oligosaccharide may be placed on a column or added directly to a preparation in a batch procedure. A preparation suspected of containing a virus is contacted with a sulfated cellulose of the present invention to allow a virus to bind to the sulfated cellulose. For example, where a sulfated oligosaccharide is added directly to a preparation, the combination is typically allowed to mix for about 30 min. at about room temperature while gently stirred. Following binding, the preparation and sulfated oligosaccharide are separated. For example, where a sulfated oligosaccharide is added directly to a preparation, the portion of the preparation which is not bound to the sulfated cellulose may be separated from the sulfated cellulose by a variety of means, including centrifugation, filtering and settling. It will be evident to those of ordinary skill in the art that the binding and separation steps may occur simultaneously. For example, where a sulfated oligosaccharide is used in a column, the preparation flows through the column to effect both binding of a virus to the sulfated oligosaccharide and separation of the portion of the preparation which is not bound.

Yet another use of a sulfated oligosaccharide of the present invention is for the delivery of a virus, such as a retrovirus, to a warm-blooded animal including humans. In one embodiment, a sulfated oligosaccharide matrix will serve as a vehicle to deliver vital antigens. For example, an unknown virus is suspected to be a low level contaminant in a product feed stream. To test for the presence of the virus, the product feed stream is first passed through a sulfated oligosaccharide column to bind and, therefore, concentrate the virus in the sample. Once bound, the viral containing sulfated oligosaccharide is directly injected into an animal (such as a rabbit) to produce antibodies. Following antibody stimulation, the serum from the incorporated animals is used to screen for the presence of known viral-specific antigens, e.g., in a traditional Western assay.

It will be appreciated by those of ordinary skill in the art, when in possession of the disclosure herein, that a sulfated oligosaccharide of the present invention has other uses. The following examples are offered by way of illustration and not by way of limitation.

EXAMPLES

EXAMPLE 1

PREPARATION OF SULFATED OLIGOSACCHARIDE

To pyridine (600 ml), chlorosulfonic acid is added dropwise (117 g) while keeping the reaction temperature below 0° C. After completing the addition, the admixture is warmed to 65° C.-70° C. To the heated admixture, 80 g of a crystalline cellulose which retains its native structure (e.g., Underivatized Hiflow Catalogue #CN 10099 manufactured by Sterogene, Arcadia, Calif.) is added. The cellulose containing admixture is maintained at 65° C.-70° C. and stirred to keep the added cellulose suspended in the liquid phase. The reaction is allowed to proceed for 4–6 hr. When the reaction is completed, the reaction mixture is cooled to 25° C. The reaction mixture is neutralized with 10% NaOH. The neutralized gel can be collected by filtration. The derivatized gel is washed with copious amounts of a buffer containing 0.2M NaCl.

The sulfated cellulose prepared above has the following characteristics. The average particle size is $5 \times 50$ $\mu$m. The activated group is sulfate ester, containing 6–9 $\mu$mol sulfate per g resin based upon titration with 0.01N NaOH. One ml of the sulfated cellulose will bind approximately $10^5$–$10^8$ colony forming units (CFU) of MLV. The cellulose is sanitizable with 0.15N NaOH and autoclavable in suspension at neutral pH for 30 min. at 120° C. The cellulose may be stored, at 4° C., pre-swollen in deionized water containing either 0.02% $NaN_3$ or 20% ethanol.

EXAMPLE 2

SULFATED OLIGOSACCHARIDE COLUMN

A. Slurry Preparation

1. An appropriate amount of gel from Example 1 is weighed out and placed in 2-3 volumes of a buffered solution (e.g., 0.1M Tris, pH 7.2) containing 0.5-3.0M salt. At regular intervals of several hours, the sulfated cellulose solution is gently stirred. This equilibration process is allowed to proceed for approximately 12 hr at room temperature. For batch processing, the gel is equilibrated with 5-10 volumes of a buffered solution containing 50 mM to <0.5M NaCl (low salt buffer).

2. The gel slurry is degassed by placing under vacuum.

B. Column Operation

1. A standard chromatography column is prepared. The outlet end of the column is closed.

2. A sufficient mount of the gel slurry, described above, is poured into the column. The actual bed height of the column is dependent on the gel capacity. The capacity of the gel is determined empirically as described above. In general, the gel should be packed into the column to a sufficient bed height so that the gel bed is not disturbed during column operation. If necessary, a filler tube, attached to the chromatography column, may be necessary for proper column packing.

3. Following column packing, 10 column volumes of desorption buffer (described below) are passed through the gel matrix at a linear velocity 25% greater than the anticipated operational rate ( 100-250 cm/h).

4. After packing the column, an appropriate column inlet is placed on the column.

5. Prior to sample application, the column is regenerated by passing 5-10 column volumes of low salt buffer (adsorption buffer). Since the column matrix is cellulose based, it is important that buffers passed over the column possess an ionic strength equivalent to at least 50 mM NACl. Solutions with lesser ionic strengths will cause the gel to swell, greatly decreasing the linear flow of solutions through the gel matrix. Following gel preparation, the column is ready for sample application.

C. Regeneration

Following the retroviral adsorption onto a column, the sulfate cellulose matrix can be regenerated by passing several volumes of a high ionic strength (2.0-3.0M) buffer (desorption buffer) through the matrix. The column should then be regenerated as described above in column operation.

Following batch retroviral adsorption, the cellulose sulfate can likewise be regenerated by exposing the matrix to a high ionic strength buffer. Following the high salt wash, the cellulose matrix can be regenerated as described above in column operation.

If the performance characteristics of the matrix are not regenerated by the high salt washes, more aggressive cleaning can be attempted by using NaOH. The cellulose matrix is not stable in high concentrations of NaOH. Therefore, the wash should not contain more than 0.15N NaOH and exposure times should not exceed 30 minutes.

EXAMPLE 3

TITER ASSAY FOR PRESENCE OF BIOLOGICALLY ACTIVE VECTOR PARTICLES IN SAMPLE 1.0 Purpose To quantify the ability of a vector test sample to transfer and express a $neo^r$ gene ("transduce") into human cells.

2.0 Principle

Recombinant retroviral "vectors" can be used to introduce DNA sequences into a target cell. It is possible to quantify the number of biologically active vector particles in a test sample by exposing a test cell line to the vector and quantifying the number of cells that have incorporated the vector DNA into their genome. Eukaryotic cells that have been transduced with a vector containing the $neo^r$ gene exhibit resistance to toxic levels of the neomycin-like antibiotic, G418. After transduction and subsequent selection in G418, individual transduced cells are allowed to grow into colony forming units that are visible to the naked eye after staining with 0.2% Coomassie Blue Stain. This allows for direct quantification of the vector's activity in terms of CFU/ml.

3.0 Scope

The test method is applicable to pre, concentrated, dialyzed, and/or post-processed materials.

4.0 References/Applicable Documents 4.1 "Gene Expression in Mice After High Efficiency Retroviral-Mediated Gene Transfer," *Science*, Vol. 230, Dec. 20, 1985.

4.2 "Transfer and Expression of Cloned Genes Using Retroviral Vectors," *Bio Techniques*, Vol. 4, No. 6 (1986).

5.0 Safety Precautions

At a minimum, the entire procedure must be performed in a laminar flow hood under sterile technique procedures. All waste should be disposed of in an appropriate manner.

6.0 Interferences 6.1 Any contamination such as fungus, bacteria or yeast that infects the cell cultures, can interfere with the assay.

6.2 Cells should be taken from 25%-75% confluent flasks to overcome any variation in transducibility or clonability of the cells due to the growth stage.

6.3 Anything that interferes with cell growth (such as residual G418 or other antibiotics) will prevent the formation of colonies.

7.0 Limits 7.1 The precision of the assay decreases as titer increases due to the need for greater dilutions, which increases the chance for random error. Independent dilutions must, therefore, be prepared in triplicate for each test sample. Test samples must be diluted to result in $\geq 10$ and $\leq 150$ colonies per 1 cm plate. Less than 10 colonies will not result in statistically significant data and will have an uncharacterized cloning efficiency. With >150 colonies, there is a substantial risk that multiple overlapping colonies will be scored as a single colony.

8.0 Materials and Equipment 8.1 10% $CO_2$ incubator 8.2 Biological Hood 8.3 Vacuum waste line 8.4 $-70°$ C. freezer 8.5 Repeat pipetter 8.6 Sterile pipettes (1, 2, 5, 10, and 25 ml)

8.7 Micropipetor (20, 200, 1000 ul)

8.8 Sterile plastic pipet tips 8.9 Sterile 6 cm tissue-culture plates 8.10 Light microscope with $10\times$ objective 8.11 Hemocytometer 8.12 96 well microtiter plates
8.13 Ice bucket
9.0 Reagents (from Sigma Chemical Co., St. Louis, Mo.; Irvine Scientific, Irvine, Calif.; or Hyclone, Logan, Utah).
 9.1 L-Glutamine 200 mM: Store below $-10°$ C.
 9.2 Hepes buffer solution 1M: Store at 2° C.-80° C.
 9.3 Non-Essential Amino Acids 100X: Store at 2° C.-8° C.
 9.4 Geniticin (G 418 stock solution) 100 mg/ml in saturated $NaHCO_3$: Store at $-20°$ C.
 9.5 Growth Media: Store at 2° C.-8° C. and use within 30 days
  500 ml Bottle Dulbecco's Modified Eagle's Medium (DME)
  50 ml Non-Irradiated, Non-Heat Inactivated Fetal Bovine Serum (FBS)
  5 ml L-Glutamine
  5 ml Hepes buffer
  5 ml Non-Essential Amino Acids
 9.6 0.2% Trypan blue solution: 0.4% Trypan Blue Stain diluted 1:2 with saline. Store at room temperature.
 9.7 G418 800 µg/ml: Add 4.52 ml of G418 stock solution to a bottle of Growth Media. Store at 2° C.-8° C. and use within 30 days.
 9.8 G418 600 µg/ml: Add 3.38 ml of G418 stock solution to a bottle of Growth Media. Store at 2° C.-8° C. and use within 30 days.
 9.10 Coomassie Blue Stain; Store at room temperature.
  10% Acetic Acid
  50% Methanol
  0.05% Coomassie Stain contains Acetic Acid and has to be used under the hood
 9.11 Polybrene 4 mg/ml: Store at 2-8° C.
 9.12 Positive control: Store concentrated master stocks in liquid $N_2$. Submaster stock is diluted 10-fold in buffer solution. Store in liquid $N_2$. To prepare working stock, dilute submaster stock 100-fold in buffer solution. Store in liquid $N_2$.
 9.13 HT1080 cells (ATCC CCL121): Thaw and use no sooner than 48 hours nor later than 30 days after thaw.
  9.13a Positive control: murine retrovirus (ATCC) able to package and produce vectors containing a selectable marker gene (e.g., bacterial TN-5 gene). See Section 4.0.
 9.14 Buffer solution
  150 mM NaCl
  25 mM Tris pH 7.2
  10 mg/ml Manitol
  1 mg/ml Albumin
Filter through a 0.45µ filter and autoclave. Prepare fresh as necessary to prepare positive control.
10.0 Procedure
 10.1 Propagating the HT1080 cell line (ATCC CCL121):
  10.1.1 HT1080 cells are a human fibrosarcoma line which is grown as a monolayer culture.
  10.1.2 ATCC guidelines suggest a split and/or media change two times weekly. See section 9.5 for growth media.
  10.1.3 Cells are to be split at a subcultivation ratio of 1:4 to 1:8 when they reach a confluent state. Do not allow cells to become past confluent.
  10.1.4 Cells should be propagated no longer than one month after a fresh thaw from the stock is received. Any changes in the characteristics of the cell line (i.e., syncitia formation, abrupt change in growth rate, etc.) noticed during this time period may require use of new cells).
  10.1.5 Splitting cells:
   1. Aspirate old growth media.
   2. Wash flask or plate with 5 mls. PBS.
   3. Apply EDTA to cells and incubate at RT or 37° C. until cells lift off of the flask surface.
   4. Pipet cells into a sterile tube, add equal volume of growth media and aliquot cells into an appropriate number of new flasks using a 1:4 or 1:8 ratio with 10 ml each growth media (see 9.5).
   5. Incubate for 24 hr. at 37° C., 10% $CO_2$.
 10.2 Day 1: Seed the Plates
  10.2.1 Harvest HT1080 cells from subconfluent (25%-75%) state. Cells should be thawed and used no sooner than 48 hours nor later than 30 days after thaw.
  10.2.2 Determine viable cell count using Trypan Blue Stain (see 9.6). For each sample to be titered, seed nine 6 cm plates at $1 \times 10^5$ viable HT 1080 cells/plate in 4 ml growth media+4 µg/ml polybrene. Label 3 plates each with sample name date and volume used to infect the plates, i.e., 4 µl, 20 µl and 100 µl.
  10.2.3 Seed three extra plates for positive control.
  10.2.4 Incubate plates for 24 hours at 37° C., 7%-10% $CO_2$.
 10.3 Day 2: Infect the Plates
  10.3.1 From known Reverse Transcriptase (RT) concentration, calculate approximate titer using the following empirical formula: titer (CFU/ml)=RT (cpm/3 µl)$\times(5 \times 10^2)$.
   Example:
    RT=20,000 cpm/3 µl
    Approx. titer=$(2 \times 10^4) \times (5 \times 10^2) = 1 \times 10^7$
  10.3.2 From approximate titer, calculate dilutions necessary to give 2.5 colonies per µl. The dilution factor will be:
   titer$\times(1/10^3)\times(1/2.5)$=dilution factor
   Example:
    Approximate titer=$10^6$ CFU/ml.
    Dilution of the sample: $(4.0 \times 10^{-4}) \times 1 \times 10^6) = 400$-fold.
  10.3.3 Serially dilute each sample 3 separate times with DMEM in 24-well microtiter plates (samples should be kept on ice at all times). Mix each dilution to homogeneity with a micropipet before transfer. A common dilution will be approx. $10^4$-fold (for a titer near $1 \times 10^8$). This can be accomplished with 2 sequential, 100-fold dilutions, i.e., A: 10 µl in 1.0 ml and 10 µl of A in 1.0 ml (a $1 \times 10^4$-fold dilution) followed by an appropriate dilution to achieve 2.5 CFU/µl as calculated in 10.3.2 (100 µl into 400 µl if the titer is $1 \times 10^8$, 100 µl into 1.2 ml of the titer is $3.0 \times 10^8$, etc.).
  10.3.4 Use 4, 20, and 100 of the final dilution to infect the plates in triplicate.

| Volume Added | Expected # of Colonies/Plate |
|---|---|
| 4 | 10 |
| 20 | 50 |

| Volume Added | Expected # of Colonies/Plate |
|---|---|
| 100 | 250 |

10.3.5 Use a 5 µl of the working positive control to infect the positive control plates in triplicate (approximately 100 CFU).

10.3.6 Incubate the plates for 24 hours at 37° C., 7%–10% $CO_2$.

10.4 Day 3: Select the Plates 10.4.1 Aspirate media from all plates using a sterile Pasteur pipet with a sterile piper tip on the end of the Pasteur piper. Change tips for each plate to avoid cross contamination of the samples.

10.4.2 Add 4 ml/plate G418 800 µg/ml media (9.7).

10.4.3 Incubate for 5 days at 37° C., 7%–10% $CO_2$.

10.5 Day 8: Refeed the Plates 10.5.1 Aspirate media from all plates using a sterile Pasteur piper with a sterile pipet tip on the end of the Pasteur piper. Change tips for each plate to avoid cross contamination of the samples.

10.5.2 Refeed the plates with 4ml/plate G418 600 µg/ml media (9.8).

10.5.3 Incubate 5 days at 37° C., 7%–10% $CO_2$.

10.6 Day 13–14: Stain the Plates 10.6.1 Aspirate the media from all plates.

10.6.2 Stain each plate with 1.5–2.0 ml of Coomassie Stain (9.10).

10.6.3 After 15–20 minutes, remove stain and carefully (to avoid dislodging colonies) rinse the plates in cool tap water.

10.6.4 Set the plates to dry at room temperature.

10.6.5 Count all blue colonies and calculate titer in CFU/ml for all plates whose triplicates average 10–100 colonies per plate (see below).

11.0 Data Analysis 11.1 Titer in CFU/ml can be calculated from equation given below:

CFU/ml = (# of Colonies/# of µl tested) × (Infection Dilution Factor) × 1000 µl/ml.

Example:

| | |
|---|---|
| Dilution factor | = 400 |
| # of Colonies | = 50 |
| Volume tested | = 20 µl |
| Titer | = 50 CFU/20 µl × 400 × 1000 |
| | = $1.0 \times 10^6$ CFU/ml |

11.2 Take the mean of all the acceptable dilutions for each sample (at least 3) and calculate standard deviation. If the standard deviation is $\geq 70\%$, repeat.

11.3 The positive control must be between $1 \times 10^4 - 8 \times 10^4$ CFU/ml, or the test must be repeated.

EXAMPLE 4

RETROVIRUS DETECTION ASSAY 1.0 Purpose

The purpose of the Standard S+/L− virus is to determine if replication competent infectious virus is present in a test sample.

2.0 Principle

The assay is based upon the empirical observation that infectious murine retroviruses generate foci on the indicator cell line, $MiCl_1$ (ATCC #CCL64.1). The $MiCl_1$ (ATCC #CCL64.1) cell line is derived form the MvlLu (ATCC CCL64) mink cell line by transduction with murine sarcoma virus (MSV). It is a nonproducer non-transformed revertant clone containing a murine sarcoma provirus (MSV). The cells form sarcomas (S+), indicating the presence of the MSV genome but does not cause leukemia (L−) indicating the absence of replication-competent virus. Infection with murine retroviruses "activates" the MSV genome in some way to trigger "transformation" which results in a microscopic foci.

3.0 Scope

This test method is applicable for testing of pre-processed and processed vector as well as tissue culture samples.

4.0 References/Applicable Documents 4.1 P. T. Peebles, *Virology* 67:288 (1975).

4.2 Bassin, R. H., N. Tuttle, and P. J. Fischinger, *Int. J. Cancer* 6:95–107.

4.2.1 Bassin, R. H., N. Tuttle, and P. J. Fischinger, *Nature* 229:564–566.

4.2.2 Coffin, Teich, Varmus, Weiss, *RNA Tumor Viruses.*

5.0 Safety Precautions 5.1 At a minimum, all procedures involved with this standard test method must be performed in the laminar flow hood in the BL-2 tissue culture laboratory under sterile technique procedures.

5.2 The positive control (and potentially test samples) contain replication-competent, infectious murine amphoteric retrovirus which can infect and replicate in human cells. Its pathogenic potential in humans is unknown and, therefore, should be used carefully.

6.0 Interferences 6.1 Mycoplasma contamination may give false negative results. Any contaminating substance, such as fungus, yeast or bacteria that infects the cell cultures, interferes with the assay. The assay should be repeated if cell cultures become contaminated.

6.2 Excess acid, metabolic by-products, or residual antibiotics (e.g., G418) will kill the cells and thus interfere with the assay, therefore, schedules for media changes must be followed throughout the assay.

6.3 Unusually high titers of amphoteric retroviral vector in the sample may interfere by competing for retroviral receptors on the cell surface, therefore a sample spiked with MA virus (interference control) is run in parallel with the test sample to demonstrate validity of the test result.

6.4 Transformed cells in a test sample (cell supernatants, for example) may generate foci and thus a false positive result. These samples must be freeze-thawed or filtered through a 0.45 µm filter to remove viable cells.

7.0 Limits 7.1 The positive control virus should be serially diluted (titrated) down to 2 focus forming units (FFU) per ml to demonstrate the lower limit of detection. The titer of the positive control has been confirmed by an independent assay wherein the titer has been determined by endpoint dilution on mus dunni cells with virus detection determined by marker rescue.

8.0 Materials and Equipment 8.1 Six well tissue culture plates.

8.2 Repeat pipetter: P1000, P200, P20.
8.3 Yellow tips and blue tips for pipetter (sterile).
8.4 Sterile pipettes; 1 ml, 5 ml, 10 ml, 25 ml.
8.5 Pasteur pipettes.
8.6 10 ml syringes and $0.45\mu$ syringe filters.
8.7 Microscope with camera attachment.
8.8 Tissue culture flow hood.
8.9 Hemacytometer.
8.10 Repeat pipetter and sterile adapters.
8.11 10% $CO_2$ incubator.
9.0 Reagents
9.1 $MiCl_1$ cell line (ATCC): Cells are thawed and used in the assay after culture for at least 24 hours and no longer than 30 days. A new vial of cells must then be thawed. After each thaw, cells should be frozen down so that the stock is not depleted.
9.2 DMEM.
9.3 Fetal bovine serum (FBS).
9.4 Trypsin.
9.5 Phosphate buffered saline (PBS).
9.6 Trypan Blue reagent.
9.7 Test Sample Preparation: Place 10 ml supernatant taken from the cell line under test into a 15 ml sterile, conical tube. Sample may be frozen at $-80°$ C. until tested. If fresh samples are to be used, filter samples through a $0.45\mu$ filter to remove any transformed cells.
9.8 Maloney Amphotrpic (MA) virus positive control: Store concentrated stock with known (confirmed) titer in liquid N2. Prepare working stock dilutions (200, 20 and 2 ffu/ml) in DME medium (9.2). Aliquot into 1.5 ml eppendorf tubes and store at $-80°$ C. up to three months.
9.9 Polybrene stock, 4 $\mu g/ml$ in medium.
10.0 Procedure
Note: Throughout this assay, always return test and negative control plates to the incubator before handling the positive and interference control issue culture plates.
10.1 Day 1
10.1.1 Prepare a cell suspension of $10^5$ $MiCl_1$ cells per 2 ml media in DMEM+10% FBS+8 $\mu g/ml$ polybrene. Remove the $MiCl_1$ cells from the stock flask as described in Section 9.1. Resuspend the cell pellet in 10 ml DMEM after spinning the cells out of the trypsin solution. Perform a cell count. Make a dilution (or concentration) of the cell suspension to $5\times10^4$ $MiCl_1$ cells/ml ($10^5/2$ ml) in DMEM+10% FBS+8 $\mu g/ml$ polybrene.
10.1.2 Seed duplicate wells of a six well tissue culture plate with 2 ml per well of the MiCll cell suspension for each test sample. Label one plate "test" and the other plate "interference".
10.1.3 Seed three wells of a separate plate as above for the negative control.
10.1.4 Seed five wells of a separate plate, as above, for the positive controls.
10.1.5 Incubate plates at 37° C. in a 10% $CO_2$ incubator for 16-24 hours.
10.2 Day 2
10.2.1 Add 1 ml of the test sample to one well on the plate labeled "test" plate and one well of the plate labeled "interference".
10.2.2 Add 1 ml of DMEM (9.2) to each of the wells labeled negative control.
10.2.3 Return the "test" and "negative" control plates to the $CO_2$ incubator.
10.2.4 Add 20 FFU of MA virus to each of the wells labeled "interference".
10.2.5 Add 2 FFU of MA virus to three positive control wells, 20 FFU to one positive control well and 200 FFU to one positive control well.
10.2.6 Return "interference" and positive control plates to the $CO_2$ incubator. Incubate all plates at 37° C. in 10% $CO_2$ for 16 to 24 hours.
10.3 Day 3
10.3.1 Place a sterile yellow tip on the end of a sterile Pasteur pipet and aspirate the medium from each well. Use a separate yellow pipet tip for each well to avoid cross contamination other samples.
10.3.2 Replace the medium with 3 ml per well of DMEM (9.2).
NOTE: Return "test" and negative control plates to the incubator before handling positive controls.
10.4 Day 7
10.4.1 Check the test for focus formation on the monolayer of cells. Check the positive control wells first to make sure that enough time has passed for initial focus formation. The transformed cells or foci appear as clustered, refractile cells that overgrow the monolayer and remain attached. After viewing each well under the microscope change the medium on each well as on Day 3 and return to the incubator. Incubate cells an additional 7 days after foci formation is observed in the positive control wells.
10.5 Day 14: Repeat Day 7. Discard cultures.
11.0 Data Analysis
11.1 The test is considered valid if all of the following apply:
 (1) All three negative controls are negative (no foci present).
 (2) At least one of the three positive controls infected with MA virus of 2 FFU exhibit foci formation.
 (3) The interference control test sample spiked with 20 FFU of MA virus must exhibit foci formation for the individual test sample. A test that does not meet all of the above criteria should be repeated.
11.2 If one or more loci are present in a test sample well, that sample is scored as positive for helper virus.

EXAMPLE 5

REMOVAL OF CONTAMINATING RETROVIRUS FROM MONOCLONAL ANTIBODY

Antibody producing murine hybridoma cells are grown in RPMI media supplemented with 15% fetal bovine serum (FBS). The antibody containing cell supernatant, which is contaminated with an adventitious murine retrovirus, is separated from the murine cells by centrifugation (5 min. at 1000×g). The cell supernatant at this point contains both monoclonal antibody and the contaminating retrovirus.

To remove the contaminating retrovirus, the cell supernatant is first filtered ($0.45\mu$) to remove cellular debris. The filtered cell supernatant, which still contains contaminating retroviruses, is then passed directly over a sulfated cellulose column prepared as described in Example 2. As a result, the murine retrovirus binds to the column matrix and the desired monoclonal antibody passes through the column matrix. At this point, the retroviral-free monoclonal antibody may be further purified using standard chromatographic techniques, including DEAE, protein A or G or gel filtration chromatography.

The removal of contaminating retrovirus may be confirmed using assays such as those described in Examples 3 and 4 above.

EXAMPLE 6

SEPARATION OF RETROVIRAL VECTOR FROM CONTAMINATING PROTEINS

A retroviral vector produced from a producer cell line, grown in a DMEM growth media supplemented with fetal bovine serum, is collected with the cell supernatant. The collected supernatant is first filtered (0.45μ) to remove cellular debris and then is passed directly onto the sulfated cellulose matrix as described in Example 2. Contaminating proteins in the cell free supernatant, such as albumin, do not bind to the matrix and pass directly through the column. Following sample application, the column is washed with a low ionic strength buffer to remove the remnants of the non-binding proteins. The retroviruses are then removed from the column by using a high ionic strength buffer (a buffered solution containing 0.5–3.0M salt). The collected retroviral vector can then be further purified by conventional chromatographic methods.

From the foregoing, it will be evident that, although specific embodiments of the invention have been described herein for purposes of illustration, various modifications may be made without deviating from the spirit and scope of the invention.

I claim:

1. A method for the purification of a retrovirus from contaminating substances, comprising the steps of:
   (a) contacting a preparation containing a retrovirus with sulfated cellulose, said sulfated cellulose having from about 6 to 15 μmoles sulfate per gram of cellulose, under conditions and for a time sufficient for said retrovirus to bind to said sulfated cellulose;
   (b) separating the portion of the preparation which is not bound to said sulfated cellulose from said sulfated cellulose; and
   (c) eluting said bound retrovirus from said sulfated cellulose, thereby recovering said retrovirus.

2. The method of claim 1 wherein said sulfated cellulose has greater than 10 μmoles sulfate per gram of cellulose.

3. A method for the removal of a retrovirus from a preparation containing a retrovirus, the method comprising the steps of:
   (a) contacting the preparation with sulfated cellulose, said sulfated cellulose having about 6 to 15 μmoles sulfate per gram of cellulose, under conditions and for a time sufficient to permit said retrovirus to bind to said sulfated cellulose; and
   (b) separating the portion of the preparation which is not bound to said sulfated cellulose from said sulfated cellulose.

4. The method of any one of claims 1 or 3 wherein said sulfated cellulose has about 6 μmoles sulfate per gram of cellulose.

5. The method of claim 3 wherein said sulfated cellulose has greater than 10 μmoles sulfate per gram of cellulose.

* * * * *